United States Patent [19]

Kligman

[11] Patent Number: 4,985,235
[45] Date of Patent: Jan. 15, 1991

[54] TREATMENT OF PERIODONTOCLASIA WITH RETINOIC ACID

[76] Inventor: Albert M. Kligman, c/o Department of Dermatology, University of Pennsylvania, 36th & Hamilton Walk, Philadelphia, Pa. 19104

[21] Appl. No.: 349,978

[22] Filed: May 8, 1989

Related U.S. Application Data

[63] Continuation of Ser. No. 227,383, Aug. 2, 1988, abandoned.

[51] Int. Cl.$^5$ .............................................. A61K 7/16
[52] U.S. Cl. ...................................... 424/49; 514/725; 514/900; 514/902
[58] Field of Search ....................... 514/900, 902, 725; 424/49

[56] References Cited

U.S. PATENT DOCUMENTS

| | | | |
|---|---|---|---|
| 3,729,568 | 4/1973 | Kligman | 424/318 |
| 3,906,108 | 9/1975 | Felty | 514/560 |
| 4,214,000 | 7/1980 | Papa | 514/494 |
| 4,247,547 | 1/1981 | Marks | 514/179 |
| 4,310,509 | 1/1982 | Berglund | 424/448 |
| 4,323,557 | 4/1982 | Rosso | 424/448 |
| 4,428,933 | 1/1984 | King | 424/93 |
| 4,443,442 | 4/1984 | Skillern | 424/127 |
| 4,603,146 | 7/1986 | Kligman | 514/559 |
| 4,649,040 | 3/1987 | Pitha | 424/10 |
| 4,699,929 | 10/1987 | Mustakallio | 514/680 |
| 4,727,088 | 2/1988 | Scott | 514/725 |

FOREIGN PATENT DOCUMENTS

| | | |
|---|---|---|
| 0271332 | 6/1988 | European Pat. Off. . |
| 1593977 | 7/1970 | France . |
| 950387 | 8/1982 | U.S.S.R. . |
| 1514469 | 6/1978 | United Kingdom . |

OTHER PUBLICATIONS

Walsh GA. 105#5525w (1986).
Walsh GA. 103#213918h (1985).
Varava GA. 101#157642h (1983).
Fedorov GA. 88#164280j (1978).
Franquin GA. 72#10433r (1969).
Jonathan F. Norris, et al., "Phenytoin-Induced Gum Hypertrophy Improved by Isotretinoin," *Int. J. Dermatol.*, vol. 26, No. 9, pp. 602-603 (1987).
Vincenzo Nazzaro, et al., "Papillon-Lefevre Syndrome," *Arch. Dermatol.*, vol. 124, pp. 533-539 (1988).
Nelson E. Driban, et al., "Papillon-Lefevre Syndrome. A Clinical and Therapeutic Contribution," *Dermatologica*, vol. 165, No. 6, pp. 653-659 (1982).
*The Merck Manual* (15th Edition 1987), Chapter 249, pp. 2333-2337.
Lindhe, J., *Textbook of Clinical Periodontology* (Munksgaard/Saunders 1983).
Khmelevskii et al., "Vliianie Vitaminov A, E, K na Pokazateli Glutationovoi Antiperekisnoi Sistemy v Tkaniakh Desny pri Parodontoze," *Vopr Pitann*, 4:54 (1985).
L. J. Walsh et al., "The in vitro Effect of Retinol on Human Gingival Epithelium," *J. Invest. Dermatol.* 85:501 (1985).
Thomas et al., *J. Am. Acad. Derm.*, 4(5) (May 1981).

*Primary Examiner*—Shep K. Rose
*Attorney, Agent, or Firm*—Panitch Schwarze Jacobs & Nadel

[57] ABSTRACT

Methods of retarding and reversing periodontoclasia and gingivitis and disorders of human gingiva over 60 years of age comprise topically applying to human gingiva retinoic acid in an amount effective to retard and reverse periodontoclasia and gingivitis where said amount is insufficient to be excessively irritating. An emollient vehicle, a toothpaste and a liquid rinse facilitating the same methods are included.

17 Claims, No Drawings

TREATMENT OF PERIODONTOCLASIA WITH RETINOIC ACID

RELATED APPLICATION

This is a continuation of U.S. patent application Ser. No. 227,383, filed Aug. 2, 1988, now abandoned.

FIELD OF THE INVINTION

The present invention relates to methods of treating disorders affecting the periodontium. More particularly, the present invention is directed to topical treatment of periodontoclasia and gingivitis.

BACKGROUND OF THE INVENTION

Periodontoolasia, the general term for degenerative and destructive diseases of the periodontium, is a pervasive problem in the human mouth, especially in those persons 60 years of age and older. The pathogenesis is complex (see generally Lindhe, J., *Textbook of Clinical Periodontology* (Munksgaard/Saunders 1985)) and may take years to manifest into more advanced stages of disease. Multiple factors combine, the most important being bacteria, which initiate plaque eventuating in gingivitis, the inflammation of the gingiva or gums. Left untreated, epi- and subgingival colonies of bacteria or plaque continue to expand, causing the condition of the gingiva to worsen from acute to chronic gingivitis. There is currently no method to stop the formation and existence of plaque other than mechanical removal by, for example, scraping with dental tools.

At the chronic stage of infection and inflammation, pockets dissect between the teeth and gingiva. Macrophages accumulate and begin to secrete prostoglandins, interleukins and collagenase, which cause inflammation and destruction of the surrounding tissues. As the lesions deepen, the gingival tissues become less able to adhere to the tooth surface and become thinner, more friable and sometimes ulcerated. A deepened gingival sulcus or pocket is formed (an overt indication used to measure the severity of periodontal disease), allowing for greater subgingival bacterial infection. This deepening of the sulcus is clinically seen as gum recession.

The bacteria typically present in the early and late stages of disease and especially in the interstitial pockets of fluid are collagenase producing. Collagenase is an enzyme that destroys the protein complex, collagen. Collagen, the protein forming collagenous fibers of the skin, tendon, ligaments, bone and all other connective tissue, is the fundamental component of the network holding together the individual tooth, the periodontium and the bone surrounding and anchoring the tooth to the bone. The collagenase produced by bacteria destroys the collagen fibers which form the periodontal ligament; the tooth loosens and falls out.

The periodontal ligament attaches the tooth to the dental alveolus. The periodontal ligament is also called the periodontal membrane, but neither term adequately describes its structure or function. In addition to providing support for the tooth, the periodontal ligament provides for nutrition of adjacent structures, proprioception and tooth eruption in the juvenile mouth. Degeneration or destruction of the periodontal ligament results in loose teeth, difficultly in mastication, general soreness and pain. As the periodontal disease progresses, alveolar bone resorption occurs, leading to tooth loss.

In many persons, generally over 60 years of age, bacterially initiated periodontoclasia may be exacerbated or periodontoclasia may be independently induced by the general deterioration of the periodontium, generally called senile atrophy, senescence or regressive change. Atrophy of tissues is a characteristic and unavoidable consequence of the aging process. In senile atrophy, skin thins and, particularly in the mucosal and periodontal tissues of the mouth, older persons experience a decrease in cardiovascular flow; mucous glands involute and glandular activity generally reduces; proliferitive or cell renewal activity slows down; blood vessels decrease in number; and the periodontium tends to become thinner, more friable, and more vulnerable to infection; hence, increased prevalence with age.

Methods of the prior art have attempted to cure periodontoclasia by using bacteriostatics, such as chlorhexidine and tetracycline. Such bacteriostatic treatments, however, do nothing to alleviate the inflammatory responses accompanying diseases of the periodontium. Chlorhexidine treatment, for example, is generally unsuitable for practical use in humans because chlorhexidine stains the teeth black. In addition, bacteriostatics have limited effectiveness, are generally not appropriately administered for long periods of time (i.e. for chronic conditions) and are best administered only at the acute stage of the disease. Because periodontal disease and regressive changes in the periodontium may occur progressively over years, bacteriostatics and do not provide adequate treatment for periodontoclasia.

Other prior methods have attempted to alleviate the inflammatory responses of the periodontium and surrounding interstices. Ibuprofen, produced by Upjohn and other manufacturers, is one example of a medication designed to alleviate inflammation, mainly in arthritis. Ibuprofen and other anti-inflammatory treatments, such as Motrin, Advil and steroids (e.g., cortisone) administration, are known to potentiate infection. However, ibuprofen barely moderates gingivitis, and results are inconsistent. Moreover, high doses, typically 1,600 to 2,400 milligrams, are required for periodontal anti-inflammatory response. Ibuprofen may be generally used at the acute stage for flare-ups, but not the chronic stage. Many patients are unsuitable candidates for ibuprofen administration because of gastric bleeding and ulceration.

Further, the prior uses of anti-inflammatories and bacteriostatics are ineffective against senile atrophy and do nothing to repair or reverse periodontoclasia in general. Antibiotics, and anti-inflammatories are generally inadequate for use as preventative therapy against degenerative and destructive disease.

Russian Patent No. 950,387, issued to Sklyar, et al., discloses the use of Vitamin A (retinol) and Vitamin E to treat tooth decay and inflammation of the mucous membranes of the oral cavity. My efforts to use retinol (0.5% by weight concentration) demonstrated that Vitamin A has no effect on periodontoclasia. It is believed that retinol is metabolized to retinal quickly when topically applied in the oral cavity and is rendered ineffective in treating periodontoclasia.

Mixtures of Vitamins A, E and K were claimed to improve the status of periodontium in Khmelevskii, et al., "Vliianie Vitaminov A, E, K na Pokazateli Glutationovoi Antiperekisnoi Sistemy v Tkaniakh Desny pri Parodontoze," *Vopr Pitan*, 4:54 (1985). These vitamins were discussed as useful antioxidants. Retinol, however, is not believed to be effective in treating periodontoclasia, as discussed above.

In view of the serious deficiencies of the prior art, it would be desirable to have methods of retarding and reversing periodontoclasia and gingivitis generally and particularly periodontoclasia and gingivitis due to senile atrophy that is safe, corrective, and usable in preventative or maintenance therapy.

BRIEF SUMMARY OF THE INVENTION

According to the present invention, periodontoclasia and gingivitis may be retarded and partially reversed by topically applying to human gingiva an amount of retinoic acid effective to retard and reverse periodontoclasia and gingivitis but in an amount insufficient to be excessively irritating to the periodontal tissues. In particular, the present invention is directed to methods of treating human gingiva over 60 years of age having disorders or disease including senile atrophy, periodontoclasia and gingivitis, by topically applying to the gingiva retinoic acid in an amount effective to induce the thickening of the gingiva, including the production of new blood vessels and new collagen, but insufficient to be excessively irritating to the periodontal tissues.

DETAILED DESCRIPTION OF THE PREFERRED EMBODIMENTS

Retinoic acid (also referred to as tretinoin or vitamin A acid) is a derivative of Vitamin A (known in the art as retinol, the alcohol form of Vitamin A), resulting where the terminal methylene group of retinol is replaced with a carboxyl group. Retinol, the Vitamin A alcohol, is derived from beta-carotene, generally found in some vegetables, such as carrots. Retinoic acid is available commercially from Johnson & Johnson, sold under the trademark "RETIN A", for treatment of acne.

Retinoic acid surprisingly retards and reverses periodontoclasia when applied topically to human gingiva. Topical application may be performed by a number of methods which will be apparent to one skilled in the art of pharmacology. In one embodiment of the present invention, retinoic acid is applied topically to the gingiva using an applicator, such as a cotton swab or a toothbrush. In another embodiment, retinoic acid is topically applied by an oral rinse. It will be apparent to one skilled in the art that other methods of topical application, including application by hand, by orthodondic appliance and by other applicators known in the art may be used in accordance with the present invention.

The dosage of retinoic acid (discussed below) required to effectively treat periodontoclasia while avoiding excessive irritation to the gingiva is surprisingly low. Accordingly, the retinoic acid should be carried in a pharmaceutically suitable vehicle, preferably a liquid vehicle in solution form.

According to one embodiment of the present invention, the retinoic acid is topically applied in an emollient vehicle which preferably comprises a pharmaceutically acceptable, non-toxic, non-irritating, orally acceptable retinoic acid carrier or solvent. Preferably, the emollient vehicle comprises glycerin (a dihydric alcohol) and propylene glycol (a polyhydric alcohol), although one skilled in the art will understand that other pharmaceutically acceptable emollient vehicles may be used in accordance with the present invention.

Glycerin exhibits greater biocompatibility than does propylene glycol. On the other hand, retinoic acid is generally more soluble in propylene glycol. In addition, propylene glycol in concentrations above about 20% by weight is known to be anti-bacterial to gram positive and negative bacteria and is also anti-fungal. It is presently preferred in accordance with the present invention that an emollient vehicle comprises glycerin in an amount of about 5% to about 50% by weight and propylene glycol in an amount of about 50% to about 95% by weight. More preferably, glycerin and propylene glycol are present in a glycerin:glycol ratio of about 20:80 by weight.

One skilled in the art will appreciate that an emollient vehicle may additionally comprise pharmaceutically acceptable, non-toxic, non-irritating, orally acceptable lubricants, flavoring agents and other suitable excipients known in the art of pharmacology.

In another embodiment of the present invention, the retinoic acid is topically applied in a liquid oral rinse. Preferably, the rinse comprises a pharmaceutically acceptable, non-toxic, orally acceptable retinoic acid solvent. It is desirable to use a rinse which effectively carries the retinoic acid to the gingiva generally and which does not adversely affect the oral cavity, such as by staining or causing excessive irritation. It may also be desirable to have a rinse which is pleasant tasting and of a palatable or potable consistency. Examples of suitable liquid oral rinse solvents include alcohol and water. Other pharmaceutically acceptable components, which may be desired in a liquid oral rinse include quaternary salts, bacteriostatics, such as erythromycin and glycerin. In one embodiment of the present invention, the liquid oral rinse comprises ethanol and water in a ratio of 50:50 by weight.

In another embodiment of the present invention, the retinoic acid is topically applied in a toothpaste. One example of a toothpaste comprises about 84.8% glycerin, about 15% Cabosil M-5, about 0.05% Tenox BHA, about 0.10% Disodium EDTA and about 0.05% retinoic acid (all percent by weight). One skilled in the art will understand that the retinoic acid may be topically applied in other toothpaste compositions known in the art accordance with the present invention.

In the practice of the present invention, the therapeutically effective amounts of retinoic acid are preferably applied in a daily dosage. The retinoic acid may be applied by cotton swab, absorbent sponge, toothbrush or by hand, for example, where an emollient vehicle or a toothpaste is used. It will be apparent to one skilled in the art that fewer or more frequent dosages may be prescribed in accordance with the present invention. Factors such as age, general condition of the periodontium, periodontal history of the individual patient and extent of the periodontoclasia or gingivitis may be considered to determine the best frequency of application for the individual patient.

The therapeutic effects of the present invention may be maintained once the periodontoclasia or gingivitis has been retarded or reversed. A reduced maintainence dosage preferably comprises topical application of the retinoic acid doses of the present invention thrice weekly. It will be understood by one skilled in the art that a reduced maintenance dosage having fewer or more frequent topical applications weekly may be practiced in accordance with the present invention.

The mucosal and periodontal tissues, whether over 60 years of age or younger, are particularly sensitive relative to, for example, exposed skin. Accordingly, it is desirable, in accordance with the present invention, to avoid excess irritation, such as stinging, dryness and soreness that may result from excess retinoic acid. Generally, with the amounts of retinoic acid in an emollient vehicle or a liquid oral rinse according to the present invention, a tingling sensation may be perceived by the patient.

Retinoic acid is used in accordance with the methods of the present invention in a therapeutically effective amount. With regard to the present invention, "therapeutically effective amount" is to be understood as the amount of retinoic acid, which will retard or reverse periodontoclasia and gingivitis and, particularly in cases of senile atrophy, induce thickening of the gingiva.

In accordance with one embodiment of the present invention, it is preferred that the therapeutically effective amount of retinoic acid is about 0.01% to about 0.5% by weight concentration. More preferably, where the retinoic acid is topically applied in an emollient vehicle, the therapeutically effective amount of retinoic acid is about 0.025% by weight concentration. One skilled in the art will recognize that factors such as age, general condition of the periodontium and sensitivity to retinoic acid, will affect the choice of retinoic acid concentrations used in accordance with the present invention, which may be greater or lower depending on the individual patient.

When retinoic acid is topically applied in a liquid oral rinse or a toothpaste, it is presently preferred that the therapeutically effective amount of retinoic acid in a liquid oral rinse is an about 0.01% to about 0.5% by weight concentration, more preferably, in an amount of about 0.05% by weight. As with retinoic acid applied in an emollient vehicle, the concentration of retinoic acid may be higher or lower as readily determined by one skilled in the art based on the individual patient.

In accordance with the present invention, retinoic acid may be used in particular to treat age-dependent disorders of human gingiva over 60 years of age such as senile atrophy-induced periodontoclasia and gingivitis. Treatment of such age-related disorders of the gingiva may be practiced in a manner similar to the treatments, concentrations and dosages described above. It is particularly appropriate in cases of senile atrophy, a natural aging process, to maintain the therapeutic effects of the present invention using a reduced maintenance dosage as described above. Such maintenance generally requires that the treatment of the present invention be continued indefinitely, i.e., a program of maintenance therapy is used because significant residual effects are not generally obtained using retinoic acid topical applications according to the present invention.

Topical application of the retinoic acid may be begun at any stage of the periodontoclasia or gingivitis. One skilled in the art will appreciate that as the condition of the periodontium becomes more chronic, the overall effectiveness of retinoic acid application is decreased. It is believed, however, that the application of retinoic acid in accordance with the present invention is effective at any stage of periodontoclasia or gingivitis. One skilled in the art will appreciate that once periodontoclasia has progressed beyond the chronic stage, surgical treatment is best advised.

The progress of treatment of periodontoclasia and gingivitis generally and particularly periodontoclasia and gingivitis due to senile atrophy according to the present invention may be monitored by techniques and analyses common in the art. Gross clinical analysis, such as probing the depth of the gingival sulcus and macroscopic examination, microscopic examination, such as biopsy analysis, and X-ray analysis are examples of conventional techniques one skilled in the art may employ to monitor the progress of treatment.

While the inventor does not wish to be bound by any particular theory, it is believed that retinoic acid interrupts the drawn-out process of periodontal disease through a combination of factors including:

(1) Retinoic acid acts as an anti-inflammatory and an anti-chronic inflammatory. The inflammation caused by gingivitis and periodontoclasia in general, has been found to be reduced after application of retinoic acid. It is believed that retinoic acid inhibits macrophage migration into granulomas.

(2) Retinoic acid inhibits the production of collagenase by macrophages. The bacteria present in plaque, dental granuloma and dissecting pockets of fluid in the interstices between the tooth and gum present in more advanced stages of periodontoclasia, also produce collagenase, which destroys the matrix of the teeth and surrounding tissues and ligaments. Retinoic acid interrupts this collagenase activity, preventing the destruction of collagen.

(3) Retinoic acid increases the proliferative activity of the epidermal cells of the periodontium. This increased activity results in a thickening of the periodontal tissues and possibly a thickening of the other mucoidal tissues of the oral cavity. Such stimulation of periodontium growth is believed to result in faster wound healing and response to infection. Moreover, it is believed that retinoic acid increases the metabolism of fibroblasts. Fibroblasts synthesize the fibers of the periodontal tissues by producing collagen and by differentiating into collagenoblasts and osteoblasts. This increased metabolism helps to rejuvenate and repair damaged periostium.

(4) Retinoic acid stimulates blood flow and promotes the formation of vascular tissues (angiogenesis) as well as lymphatic tissues and cells. As a result, there is a greater capacity for the surrounding periodontal tissues to be nourished; cell mediated immune responses occur more readily; and toxins and irritants may be carried away more quickly.

No other pharmaceutical agent has these multiple effects, all of which are beneficial to retard and reverse periodontoclasia and gingivitis.

It is believed that once the periodontal ligaments have been attacked and destroyed and alveolar bone begins to be resorbed, application of retinoic acid is largely ineffective. However, retinoic acid treatment before these advanced stages of chronic periodontoclasia is believed to effectively retard and reverse degeneration and destruction. Maintenance with a reduced dosage is believed to prevent further damage and disease from occurring and to continually induce the thickening of the gingiva, especially in cases of natural senile atrophy.

In an uncontrolled experiment, forty-six women over 60 years of age having indications of chronic periodontal disease and alveolar bone atrophy were treated at the Aging Skin Clinic in Philadelphia, Pennsylvania. Over a period of about four to nine months, retinoic acid (between about 0.01% to about 0.5% by weight but mainly using about 0.025% by weight) dissolved in a glycerin/propylene glycol vehicle in an about 20:80 by weight ratio was topically applied to the gingiva by cotton swabs. Application occurred once daily after brushing the teeth.

Eight women having about the same periodontal condition described above were similarly treated using the glycerin/polypropylene glycol vehicle alone without retinoic acid.

Approximately 80% of the women treated with retinoic acid reported palpable benefits, including an increased bulk of the gingiva, reduced gingival recession and less gingival sensitivity and bleeding. The gingiva in these women appeared less friable and were less pale and more pinkish-red. Additionally, some women reported a decrease in mouth odor; probably due to decreased activity of sulfide-producing bacteria.

In approximately 30% of the women treated with retinoic acid, there was an observable decrease in the depth of the sulcus surrounding the teeth.

The women treated with the vehicle, only, experienced no change in their chronic gum condition. One woman thought some improvement had occurred; none was observed.

The present invention may be embodied in other specific forms without departing from the spirit or essential attributes thereof and, accordingly, reference should be made to the appended claims, rather than the specification, as indicating the scope of the invention.

I claim:

1. A method of retarding and reversing periodontoclasia and gingivitis, which comprises topically applying to human gingiva retinoic acid in an amount and for a period of time effective to retard and reverse said periodontoclasia and gingivitis, said amount being insufficient to be excessively irritating.

2. The method according to claim 1, wherein the retinoic acid is present in an emollient vehicle.

3. The method according to claim 2, wherein the emollient vehicle comprises polyhydric alcohol.

4. The method according to claim 2, wherein the emollient vehicle comprises a mixture of glycerin and propylene glycol.

5. The method according to claim 4, wherein glycerin is present in an amount of about 5% to about 50% by weight.

6. The method according to claim 4, wherein propylene glycol is present in an amount of about 50% to about 95% by weight.

7. The method according to claim 4, wherein the ratio of glycerin to propylene glycol is about 20:80 by weight.

8. The method according to claim 1, wherein the retinoic acid is present in a liquid oral rinse.

9. The method according to claim 8, wherein the rinse comprises a non-toxic, orally acceptable, aqueous solvent for said retinoic acid.

10. The method according to claim 8, wherein the rinse comprises ethanol and water in a ratio of about 50:50 by weight.

11. The method according to claim 1, wherein the amount of retinoic acid is an about 0.01% to about 0.5% by weight concentration.

12. The method according to claim 2, wherein the amount of retinoic acid in the emollient vehicle is an about 0.025% by weight concentration.

13. The method according to claim 8, wherein the amount of retinoic acid in the liquid oral rinse is an about 0.05% by weight concentration.

14. The method according to claim 1, wherein the retinoic acid is applied in a daily dosage.

15. A method of treating disorders of human gingiva over 60 years of age, said disorders selected from the group consisting of senile atrophy, periodontoclasia and gingivitis, which comprises topically applying to the gingiva retinoic acid in an amount and for a period of time effective to induce thickening of the ginviva but insufficient to be excessively irritating.

16. A method of preventing recurrence of periodontoclasia and gingivitis in patients in which the periodontoclasia and gingivitis has been retarded and reversed, comprises topically applying to human gingiva of said patients retinoic acid in an amount and for an indefinite maintenance period of time effective to prevent further damage and disease from occurring due to periodontoclasia and gingivitis, said amount being insufficient to be excessively irritating.

17. The method according to claim 16 wherein said indefinite maintenance period of time comprises topical application of said retinoic acid about thrice weekly.

* * * * *